(12) United States Patent
Herner et al.

(10) Patent No.: US 11,499,310 B2
(45) Date of Patent: Nov. 15, 2022

(54) GAIT ASSISTANCE SLAB

(71) Applicant: Honda Motor Co., Ltd., Tokyo (JP)

(72) Inventors: Don Herner, Tustin, CA (US); Charles Eddy, Rancho Palos Verdes, CA (US); Daniel B. Gast, Torrance, CA (US)

(73) Assignee: Honda Motor Co., Ltd., Tokyo (JP)

( * ) Notice: Subject to any disclaimer, the term of this patent is extended or adjusted under 35 U.S.C. 154(b) by 498 days.

(21) Appl. No.: 16/830,868

(22) Filed: Mar. 26, 2020

(65) Prior Publication Data

US 2021/0301524 A1 Sep. 30, 2021

(51) Int. Cl.
*E04B 5/02* (2006.01)
*A61B 5/11* (2006.01)
*A61B 5/00* (2006.01)
*A61H 3/00* (2006.01)

(52) U.S. Cl.
CPC .............. *E04B 5/026* (2013.01); *A61B 5/112* (2013.01); *A61B 5/1122* (2013.01); *A61B 5/1123* (2013.01); *A61B 5/1128* (2013.01); *A61B 5/4538* (2013.01); *A61H 3/00* (2013.01); *A61B 2560/0204* (2013.01); *A61B 2562/0219* (2013.01); *A61B 2562/0247* (2013.01); *A61B 2562/0252* (2013.01); *A61H 2003/001* (2013.01); *A61H 2201/5058* (2013.01); *A61H 2201/5071* (2013.01)

(58) Field of Classification Search
CPC . E04B 5/026; A61B 5/112; A61H 3/00; A63F 13/214; A43B 3/34
See application file for complete search history.

(56) References Cited

U.S. PATENT DOCUMENTS 7,219,449 B1 * 5/2007 Hoffberg .............. A43B 3/0026
36/88
7,304,416 B2 12/2007 Mullen
2008/0134541 A1 * 6/2008 Bar-Haim ................ A43B 3/34
36/27
(Continued)

FOREIGN PATENT DOCUMENTS

CN 105126328 A 12/2015
WO 2012080636 A1 6/2012
(Continued)

*Primary Examiner* — Samchuan C Yao
*Assistant Examiner* — Nathan M Le
(74) *Attorney, Agent, or Firm* — Aaron Fong; American Honda Motor Co., Inc.

(57) ABSTRACT

A gait assistance slab is provided. The gait assistance slab includes a body that includes an outer surface. The gait assistance slab further includes a plurality of sensors disposed inside the body. The gait assistance slab further includes a plurality of actuators disposed inside the body. The gait assistance slab further includes circuitry communicatively coupled to the plurality of sensors and the plurality of actuators. The circuitry detects a presence of a person on the outer surface based on an electric signal acquired from one of the plurality of sensors. The circuitry determines a level of actuation of one of the plurality of actuators based on the detected presence of the person and the acquired electric signal. The circuitry further controls, based on the determined level of actuation, the one of the plurality of actuators to assist gait of the person on the outer surface.

14 Claims, 7 Drawing Sheets

(56) References Cited

U.S. PATENT DOCUMENTS

| | | | |
|---|---|---|---|
| 2011/0054359 A1* | 3/2011 | Sazonov | A61B 5/1118 600/595 |
| 2013/0154441 A1 | 6/2013 | Redmond | |
| 2014/0310981 A1* | 10/2014 | Abshire | A43B 7/1425 36/28 |
| 2018/0217662 A1* | 8/2018 | Smoot | A63B 24/0021 |

FOREIGN PATENT DOCUMENTS

| | | | |
|---|---|---|---|
| WO | 2016102864 A1 | 6/2016 | |
| WO | WO-2019058380 A1 * | 3/2019 | A43B 13/143 |

\* cited by examiner

GAIT ASSISTANCE SLAB

BACKGROUND

Variety of advancements have been observed in the field of energy harvesting from floor slabs or floor carpets. In certain situations, the floor slabs may include various sensors which may harvest energy from objects passing over the floor slabs. The objects may include, a person, a vehicle, or a cargo, and the like. The objects may generate mechanical vibrations while passing over the floor slabs. The sensors in the floor slabs may acquire such mechanical vibrations and may convert them into electrical energy, as the harvested energy. As the sensors in the floor slabs are configured to absorb such mechanical vibrations/energy from the walking motion of the person, the absorption of energy may induce walking fatigue on the person passing over the floor slabs. Such walking fatigue may not be desired by the person, especially with certain medical conditions, such as obesity, or pregnancy, or low blood pressure, and the like. Thus, there is a need to enhance floor slabs which may reduce walking fatigue and provide real-time gait assistance to the person or other objects passing over the floor slabs.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

An exemplary aspect of the disclosure provides a gait assistance slab. The gait assistance slab may include a body. The body may include an outer surface. The gait assistance slab may further include a plurality of sensors disposed inside the body. The gait assistance slab may further include a plurality of actuators disposed inside the body. The gait assistance slab may further include circuitry communicatively coupled to the plurality of sensors and the plurality of actuators. The circuitry may be configured to acquire an electric signal from one of the plurality of sensors. The circuitry may be further configured to detect a presence of a person on the outer surface based on the electric signal acquired from one of the plurality of sensors. The circuitry may be further configured to determine a level of actuation of one of the plurality of actuators based on the detected presence of the person and the electric signal acquired from the one of the plurality of sensors. The circuitry may be further configured to control, based on the determined level of actuation, the one of the plurality of actuators to assist gait of the person on the outer surface.

Another exemplary aspect of the disclosure provides an electronic device. The electronic device may include circuitry that may be configured to receive an electric signal acquired from one of a plurality of sensors disposed inside a body of a gait assistance slab. The body may include an outer surface. The circuitry may be further configured to detect a presence of a person on the outer surface based on the received electric signal acquired from the one of the plurality of sensors. The circuitry may be further configured to determine a level of actuation of one of a plurality of actuators disposed inside the body of the gait assistance slab. The circuitry may be further configured to transmit information about the determined level of actuation to the gait assistance slab. The gait assistance slab may control the one of the plurality of actuators based on the received information to assist gait of the person on the outer surface.

Another exemplary aspect of the disclosure provides a method for gait assistance. A computing device, for example, a gait assistance slab, may execute operations of the method. The gait assistance slab may include a body with an outer surface, a plurality of sensors that may be disposed inside the body, a plurality of actuators that may be disposed inside the body, and circuitry that may be communicatively coupled to the plurality of sensors and the plurality of actuators. The method may include acquiring, by the circuitry, an electric signal from one of the plurality of sensors. The method may further include detecting, by the circuitry, a presence of a person on the outer surface based on the acquired electric signal from the one of the plurality of sensors. The method may further include determining, by the circuitry, a level of actuation of the one of the plurality of actuators based on the detected presence of the person and the electric signal acquired from the one of the plurality of sensors. The method may further include, controlling, by the circuitry, the one of the plurality of actuators based on the determined level of actuation to assist gait of the person on the outer surface.

This summary is provided to introduce a selection of concepts in a simplified form that are further disclosed in the detailed description of the present disclosure. This summary is not intended to identify key or essential inventive concepts of the claimed subject matter, nor is it intended for determining the scope of the claimed subject matter.

Figure 1:
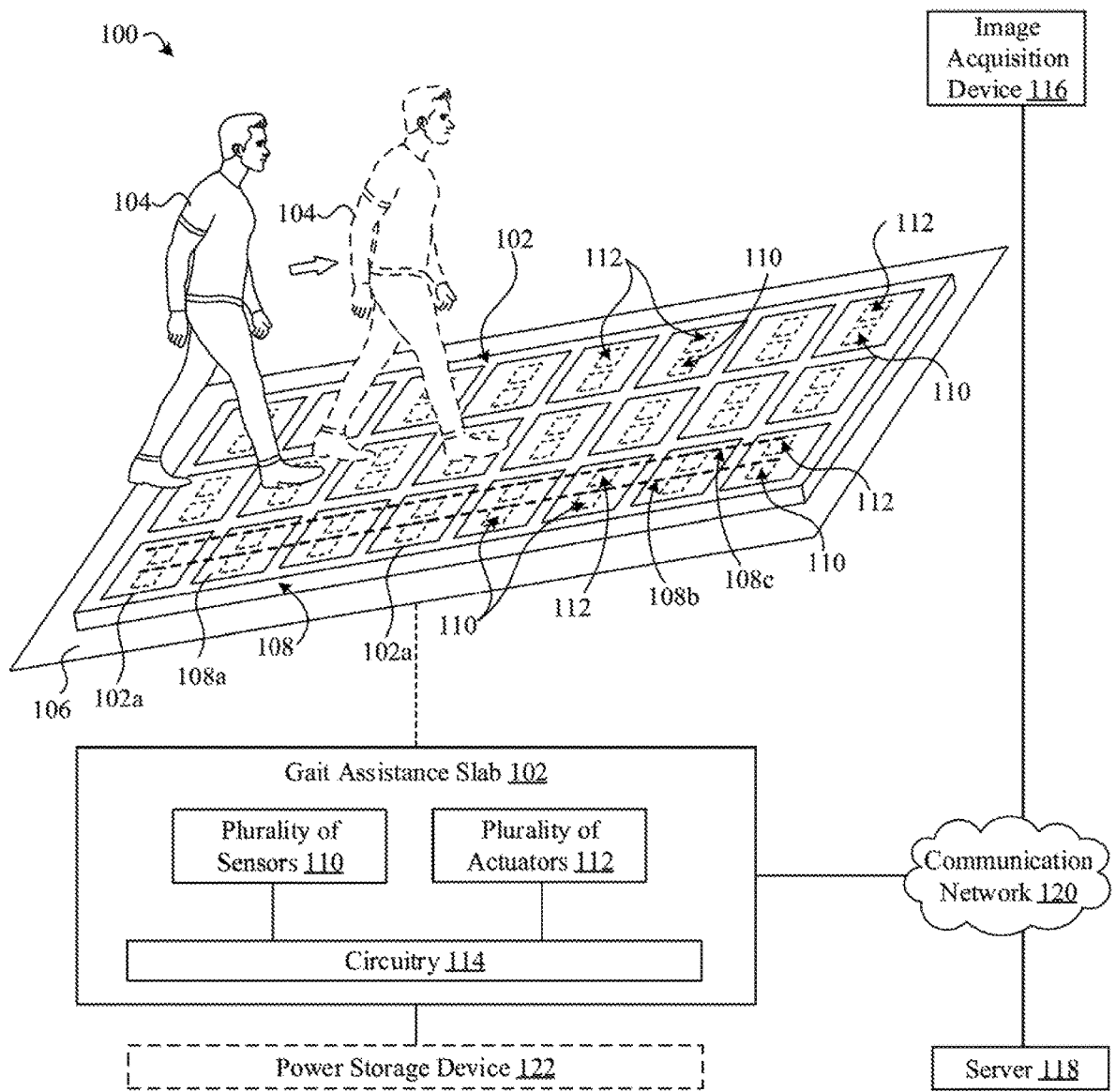
FIG. 1 is a block diagram that illustrates an exemplary network environment including an exemplary gait assistance slab, in accordance with an embodiment of the disclosure.

The foregoing summary, as well as the following detailed description of the present disclosure, is better understood when read in conjunction with the appended drawings. For the purpose of illustrating the present disclosure, exemplary constructions of the preferred embodiment are shown in the drawings. However, the present disclosure is not limited to the specific methods and structures disclosed herein. The description of a method step or a structure referenced by a

DETAILED DESCRIPTION

The following described implementations may be found in a gait assistance slab to provide a gait assistance to an object that may pass over the gait assistance slab (for example a gait assistance carpet). For example, the object may be a person who may be walking on the gait assistance slab. In certain instances, the object may be even a light weight vehicle, or a cargo, and the like. Exemplary aspects of the disclosure may provide a gait assistance slab, which may be deployed on a floor, so that when a person (or any light-weight object, for example, a bicycle) walks on the gait assistance slab, the disclosed gait assistance slab may be configured to assist gait of the person. The gait assistance slab (or a gait assistance carpet) may include a body with an outer surface, a plurality of sensors, and a plurality of actuators.

The gait assistance slab may be configured to enclose the plurality of sensors and the plurality of actuators inside the body. The plurality of sensors (for example, piezoelectric sensors) may be configured to generate an electric signal when the person walks on the outer surface of the body of the gait assistance slab. Based on the generated electric signal, the gait assistance slab may be configured to detect the presence of the person on the outer surface. Based on the detected presence of the person, the gait assistance slab may be further configured to determine a level of actuation for one of the plurality of actuators. The level of actuation may correspond to a particular height or speed of lift of one of the plurality of actuators. Based on the determined level of actuation, the gait assistance slab may be further configured to control one of the plurality of actuators to assist gait of the person on the outer surface. The control of one of the plurality of actuators may include a lift or a retraction of one of the plurality of actuators, which may further lift or retract a portion of the outer surface of the gait assistance slab. When the portion of the outer surface of the gait assistance slab is lifted-up, the person walking on the portion of the outer surface may experience a real-time leverage from the outer surface, which may further ease the walk of the person. Such real-time leverage or assistance provided from the outer surface of the gait assistance slab may reduce walking fatigue of the person when the person walks on the gait assistance slab. Further, the real-time leverage or gait assistance provided from the outer surface of the gait assistance slab may further enhance walking speed for a faster movement of the person over the disclosed gait assistance slab.

The disclosed gait assistance slab may be further configured to monitor several factors associated with the walking person and assist the walking person in accordance with the monitored factors. For example, such factors may include, but not limited to, a medical condition (such as a weight of the person or a pregnancy status of the person, and the like), emotional characteristics of the person, a physical condition (such as, a speed of movement of the person), an uphill or downhill situations, or a traffic of other people crowded in a path of the walking person, and the like). Based on the monitored medical and/or physical condition, the gait assistance slab may be configured to control the actuations of the plurality of actuators, to further reduce walking fatigue, improve comfort of the person, and provide real-time gait assistance to the person (or other objects) moving over the gait assistance slab.

Reference will now be made in detail to specific aspects or features, examples of which are illustrated in the accompanying drawings. Wherever possible, corresponding or similar reference numbers will be used throughout the drawings to refer to the same or corresponding parts.

FIG. 1 is a block diagram that illustrates an exemplary network environment with an exemplary gait assistance slab, in accordance with an embodiment of the disclosure. With reference to FIG. 1, there is shown an exemplary network environment 100. The exemplary network environment 100 may include a gait assistance slab 102 that may be configured to assist gait of a person 104 present on the gait assistance slab 102. The gait assistance slab 102 may be placed on a floor 106 of an enclosed or open space. The enclosed or open space may include, but is not limited to, a room, a road, a walkway, a walking track, or a passenger boarding bridge. The gait assistance slab 102 may include a body 108, a plurality of sensors 110 and a plurality of actuators 112 disposed inside the body 108. The gait assistance slab 102 may further include circuitry 114 that may be communicatively coupled to the plurality of sensors 110 and the plurality of actuators 112. The exemplary network environment 100, shown in FIG. 1, may further include an image acquisition device 116, a server 118, a communication network 120, and a power storage device 122 that may be coupled to the gait assistance slab 102. The communication network 120 may facilitate communication between the circuitry 114, the image acquisition device 116, and the server 118.

The gait assistance slab 102 may be disposed on the floor 106 in a specific configuration to assist gait of the person 104. The specific configuration may include, but not limited to, a carpet configuration, a tile configuration, a laminate configuration, or a mat configuration. The gait assistance slab 102 may include a plurality of components (for example, the plurality of sensors 110 or the plurality of actuators 112) that may be disposed inside the body 108 to assist gait of the person 104, when the person 104 is present or walks over the gait assistance slab 102. In an embodiment, in order to assist gait of an object (for example, the person 104), the gait assistance slab 102 may be configured to detect a presence of the person 104 on an outer surface (for example, an outer surface 108a of the body 108) of the gait assistance slab 102 based on an electric signal acquired from one of the plurality of sensors 110. Based on the detected presence of the person 104 and the electric signal acquired from one of the plurality of sensors 110, the gait assistance slab 102 may be further configured to determine a level of actuation for one of the plurality of actuators 112. Based on the determined level of actuation, the gait assistance slab 102 may be further configured to control (i.e. lift or retract) one of the plurality of actuators 112 to assist gait of the person 104 on the outer surface 108a. The details of the detection of presence of the person 104, determination of the level of actuation, or the control of the actuator is described in detail, for example, in FIG. 3.

The gait assistance slab 102 may also be configured to monitor several conditions or factors associated with the walking person 104 and assist the walking person 104 in accordance with such monitored factors. For example, such factors may include, but not limited to, a medical condition (such as a weight of the person 104 or a pregnancy status of the person 104), an emotional condition of the person 104, a physical condition (such as, a speed of movement of the person 104, an uphill or downhill situations, a traffic of other persons crowded in a path of the walking person 104, and the like). Based on the monitored medical, emotional, or physical conditions, the gait assistance slab 102 may be configured to control the actuations of the plurality of actuators 112 to further reduce walking fatigue and improve comfort and gait of the person 104. The details of such monitored factors and control of the plurality of actuators 112 are described in detail, for example in FIGS. 4, 5A-5B, and 6.

In an embodiment, the gait assistance slab 102 may include a plurality of tiles 102a. The plurality of tiles 102a may be arranged in a tiled pattern to form the outer surface 108a of the gait assistance slab 102, as shown in FIG. 1. In FIG. 1 of the present disclosure, the plurality of tiles 102a are shown to have a substantially square profile, as an example. One skilled in the art may understand that, the plurality of tiles 102a may have any structural profile, which may include, a rectangular profile, a circular profile, and the like, without deviation from the scope of the disclosure. It may be noted that the number of plurality of tiles 102a of the gait assistance slab 102 shown in FIG. 1 is presented merely as an example. The gait assistance slab may also include only one tile or more than one tile, to assist gait of the person 104, without deviation from the scope of the disclosure. For example, the gait assistance slab 102 may include only one tile to provide gait assistance to the person 104 for a short-distance travel (for example, distance less than 1 feets, yard, or meter). In other example, the gait assistance slab 102 may include the plurality of tiles 102a for a long-distance travel (for example, in certain feets, yards, or meters). Similarly, the positions and/or the arrangements of the plurality of tiles 102a shown in FIG. 1 is merely presented as example. The present disclosure may also be applicable to other positions or arrangement of the plurality of tiles 102a of the gait assistance slab 102, without deviation from the scope of the disclosure.

In an embodiment, the gait assistance slab 102 may be removably coupled to the floor 106 to improve modularity in construction between the gait assistance slab 102 and the floor 106. In other embodiment, the gait assistance slab 102 may be integrally fixed to the floor 106 to reduce wear and tear and to improve service life of the gait assistance slab 102. It may be noted that the floor 106 shown in FIG. 1 is presented merely as an example of a pathway for the person 104. The present disclosure may be also applicable to other types of pathway, such as a building floor, a stairway, a walkway, or even a passenger boarding bridge, and the like. The description of other types of the pathway has been omitted from the disclosure for the sake of brevity.

The person 104 may be a pedestrian who may walk over the gait assistance slab 102 during a journey. It may be noted that the person 104 shown in FIG. 1 is presented merely as an example of the object. The present disclosure may be also applicable to other types of the object, such as, but not limited to, any living entity (such as a human, an animal, and the like), or any non-living entity, (such as, a vehicle, a cargo, and the like). The description of other types of the object has been omitted from the disclosure for the sake of brevity.

The body 108 of the gait assistance slab 102 may have a suitable structure and design that may be configured to enclose the plurality of sensors 110 and the plurality of actuators 112. The body 108 may have a substantially square or a rectangular profile as shown in FIG. 1, so that, a plurality of gait assistance slabs (for example the gait assistance slab 102) may be easily installed on the floor 106 without any gaps or any interference wear between the gait assistance slabs, as compared to other structural profile of the body 108, such as circular profile that may form gaps during installation of the plurality of gait assistance slabs on the floor 106. It may be noted that the substantially square or a rectangular profile of the body 108 shown in FIG. 1 is presented merely as an example of a structural profile of the body 108. The present disclosure may be also applicable to other types of the structural profile of the body 108, such as a hexagonal structural profile, or an octagonal structural profile and the like. The description of other types of structural profile of the body 108 has been omitted from the disclosure for the sake of brevity.

In an embodiment, the outer surface 108a of the body 108 may be made up of a resilient material. For example, the resilient material may be a rubber material, a plastic material, and the like. As the outer surface 108a of the body 108 is made up of the resilient material, the outer surface 108a may deform and reset in accordance with the contact of the person 104. For example, when the person 104 walks on the outer surface 108a or on any of the plurality of tiles 102a, the outer surface 108a may be configured to deform and apply pressure on the plurality of sensors 110 to generate the electric signal. Further, when the person 104 moves away from the outer surface 108a or from one of the plurality of tiles 102a, the outer surface 108a may be configured to reset from the deformation and release the pressure applied on the plurality of sensors 110.

The plurality of sensors 110 may include a suitable structure, circuitry, and/or interface that may be disposed inside the body 108. The plurality of sensors 110 may be in contact with the outer surface 108a to receive the contact pressure of the person 104 when the person 104 is present or walk over the gait assistance slab 102. In an embodiment, the plurality of sensors 110 may correspond to piezoelectric sensors that may be arranged in a first pattern 108b inside the body 108, as shown in FIG. 1. One skilled in the art may understand that, the first pattern 108b is merely an example and the plurality of sensors 110 may be arranged at any pattern inside the body 108. Each of the plurality of sensors 110 may be configured to individually generate the electric signal when the pressure is exerted on a surface of the corresponding sensor of the plurality of sensors 110. Thus, when the person 104 is present or walks on the outer surface 108a of the body 108, the corresponding sensor of the plurality of sensors 110 may be triggered based on the applied pressure and may further generate the electric signal in accordance with the applied pressure. Each of the plurality of sensors 110 may be configured to detect a change of the pressure, acceleration or force applied based on the movement of the person 104 and convert the applied pressure or force to the corresponding electric signal. The plurality of sensors 110 may be further configured to provide the generated electric signal to the circuitry 114 of the gait assistance slab 102 to further determine the presence or contact of the person 104. The plurality of sensors 110 may also provide the generated electric signal to the power storage device 122 for storage of the electric signal and the corresponding electric power. Examples of the plurality of sensors 110 may include, but are not limited to, a piezoelectric sensor, a pressure sensor, a load cell, an acceleration sensor, an impact sensor, and the like.

The plurality of actuators 112 may include a suitable structure, circuitry, and/or interface that may be disposed inside the body 108. In an embodiment, the plurality of actuators 112 may be arranged in a second pattern 108c inside the body 108 as shown in FIG. 1. In an embodiment, each of the plurality of actuators 112 may be placed close to at least one sensor of the plurality of sensors 110 as shown in FIG. 1. For example, each of the plurality of tiles 102a may include at least one sensor and one actuator based on a size of a tile of the plurality of tiles 102a. The plurality of actuators 112 may be configured to lift or retract based on a command or a control signal received from the circuitry 114. In one embodiment, each of the plurality of actuators 112 may be selectively activated and may be lifted-up based on the signal or the command received from the circuitry 114, to leverage the gait of the person 104. In other embodiment, each of the plurality of actuators 112 may be selectively deactivated and retracted down based on the control or the signal received from the circuitry 114. It may be noted that the plurality of actuators 112, shown in FIG. 1, is presented merely as an example of an actuator to assist gait of the person 104. The present disclosure may be also applicable to other types of actuator, such as a mechanical actuator, an electro-mechanical actuator, a hydraulic actuator, or a pneumatic actuator, and the like. The description of other types of actuators has been omitted from the disclosure for the sake of brevity.

The circuitry 114 may include suitable logic, circuitry, and interfaces that may be configured to execute program instructions associated with different operations to be executed by the gait assistance slab 102. The circuitry 114 may be communicatively coupled to the plurality of sensors 110 and the plurality of actuators 112 and may control different operations to be executed by the gait assistance slab 102. For example, some of the operations may include, but not limited to, acquisition of the electric signal from at least one of the plurality of sensors 110, detection of the presence of the person 104 on the outer surface 108a of the body 108 based on the generated electric signal, determination of the level of actuation of one of the plurality of actuators 112 based on the detected presence of the person 104 and the electric signal acquired from the one of the plurality of sensors 110, and control of the one of the plurality of actuators 112 based on the determined level of actuation to assist gait of the person 104 on the outer surface 108a of the body 108.

The circuitry 114 may include one or more specialized processing units, which may be implemented as a separate processor. In an embodiment, the one or more specialized processing units may be implemented as an integrated processor or a cluster of processors that perform the functions of the one or more specialized processing units, collectively. The circuitry 114 may be implemented based on a number of processor technologies known in the art. Examples of implementations of the circuitry 114 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), a Programmable Logical Control (PLC) Unit, and/or other control circuits. In an embodiment, the circuitry 114 may be further configured to control or communicate with the image acquisition device 116 to acquire medical, emotional, or gait information of the person 104.

Figure 5A:
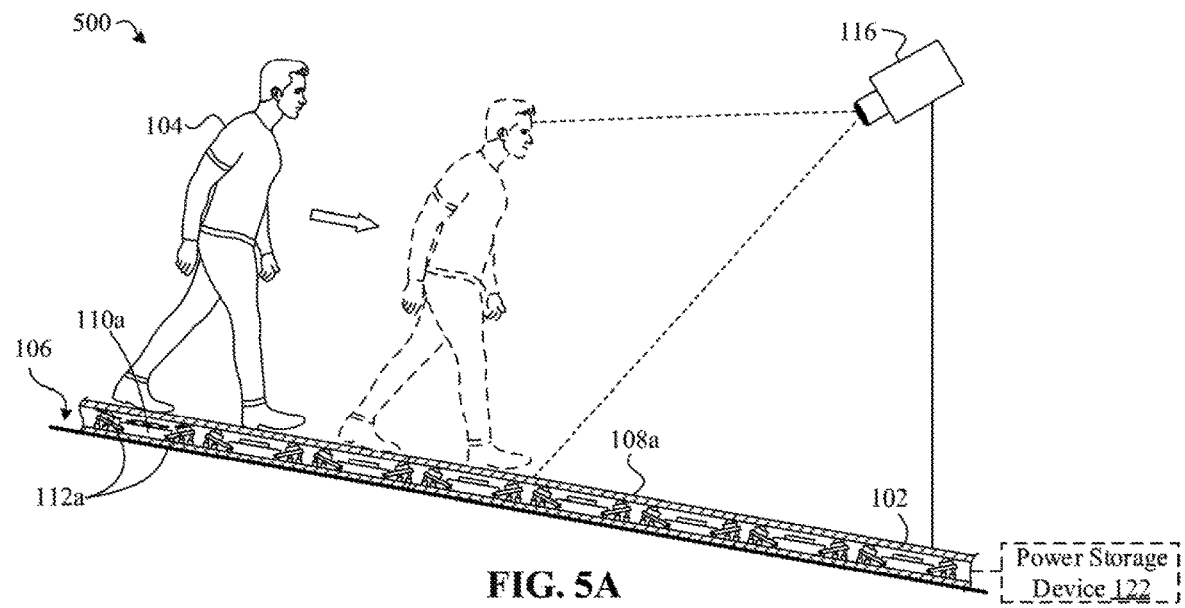
FIGS. 5A and 5B are diagrams that collectively illustrate an exemplary scenario of gait assistance on an inclined surface, by the gait assistance slab of FIG. 1, in accordance with an embodiment of the disclosure.
Figure 5B:
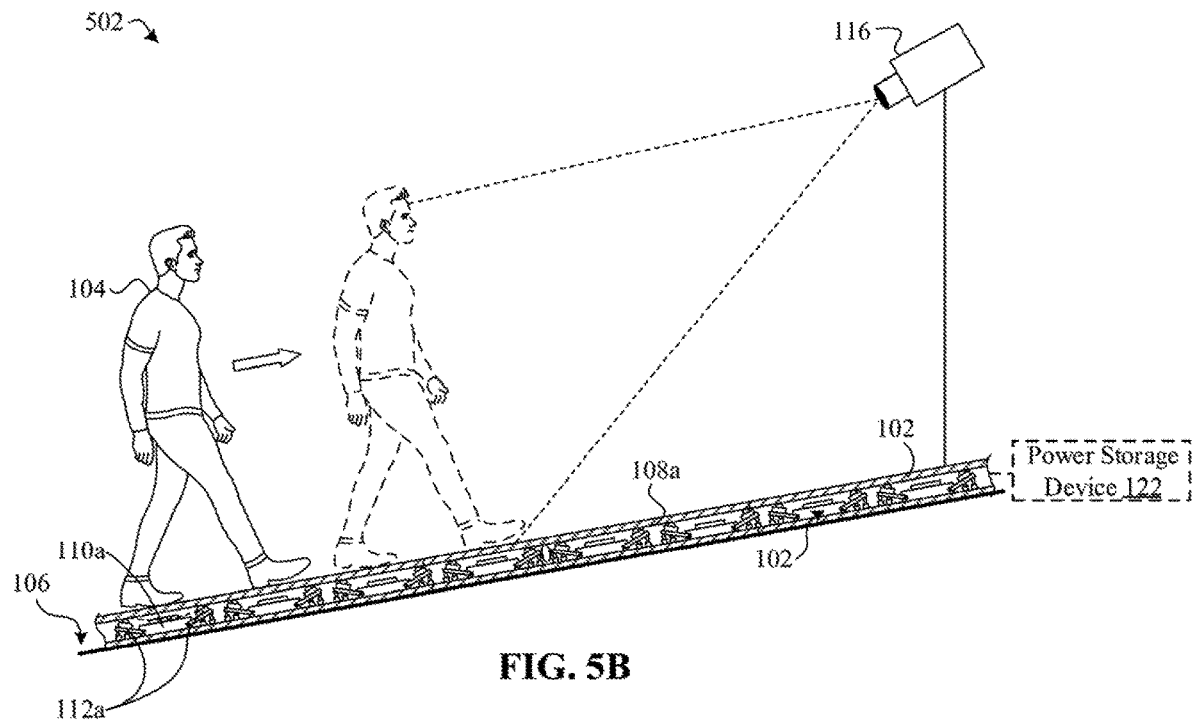

The image acquisition device 116 may include a suitable logic, circuitry, and/or interfaces that may be configured to acquire a plurality of images of the person 104 present on the outer surface 108a of the body 108. The image acquisition device 116 may be further configured to transmit the acquired plurality of images of the person 104 to the circuitry 114 through the communication network 120. In an embodiment, the image acquisition device 116 may also be configured to acquire an image of the gait assistance slab 102 to determine a presence of the gait assistance slab 102 on an inclined surface (as shown in FIGS. 5A-5B) of the floor 106. Examples of the image acquisition device 116 may include, but are not limited to, an image sensor, a wide-angle camera, an action camera, a closed-circuit television (CCTV) camera, a camcorder, a digital camera, camera phones, a time-of-flight camera (ToF camera), a night-vision camera, and/or other image capture devices.

The server 118 may include suitable logic, circuitry, interfaces, and/or code that may be configured to continuously record a log of the control signal from the circuitry 114. The log of the control signal may relate to the control of the movement (i.e., the lift and retraction) of the plurality of actuators 112. The server 118 may be further configured to continuously record the plurality of images of the person 104 and/or the gait assistance slab 102, which may be acquired from the image acquisition device 116. In certain scenario, the gait assistance slab 102 may have some technical problems, such as, one of the plurality of the sensors 110, or one of the plurality of the actuators 112, or the body 108 of the gait assistance slab 102 may be stalled, or may work in an intermittent manner. To troubleshoot such problems, the circuitry 114 may be configured to access the recorded log of the server 118 and may be configured to perform diagnostics to automatically identify an abnormality that relates to one of the plurality of the sensors 110, or one of the plurality of the actuators 112, or the body 108 of the gait assistance slab 102. For example, the abnormality may relate to a faulty actuator (not shown) from the plurality of actuators 112 that may be working in the intermittent manner, or even stalled because of a technical failure. Once the faulty actuator is identified from the plurality of actuators 112, an operator or a vendor (not shown) may repair the faulty actuator or replace the faulty actuator with a functional actuator. In an embodiment, the server 118 may store contact details of such operator or vendors. The server 118 may provide the stored contact details to the gait assistance slab 102 based on a request received from the gait assistance slab 102 or based on an analysis of the recorded log of the control of the plurality of sensors 110 or the plurality of actuators 112. In some embodiments, the server 118 may be implemented as a cloud server, which may be utilized to execute various operations through web applications, cloud applications, HTTP requests, file transfer, and the like. Examples of the server 118 may include, but are not limited to, an application server, a diagnostic server, a cloud server, a web server, a database server, a file server, a mainframe server, or a combination thereof.

The communication network 120 may include a communication medium through which the gait assistance slab 102, the image acquisition device 116, and the server 118 may communicate with each other. The communication network 120 may be one of a wired connection or a wireless connection Examples of the communication network 120 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the exemplary network environment 100 may be configured to connect to the communication network 120 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

The power storage device 122 may include suitable logic, circuitry, and/or interfaces that may be configured to store the electric signal generated from the plurality of sensors 110 due to the presence of the person 104 or other objects (for example, bicycle) on the outer surface 108a of the gait assistance slab 102. In some embodiments, the power storage device 122 may be a source of electric power for one or more electric circuits or loads. For example, the power storage device 122 may be coupled to the gait assistance slab 102 and provide the electrical power (i.e., the electric signal) to at least one of the plurality of sensors 110, the plurality of actuators 112, the circuitry 114, or the image acquisition device 116. In some embodiments, the power storage device 122 may be integrated inside the gait assistance slab 102. In an embodiment, the power storage device 122 may be a rechargeable battery. In some embodiments, the power storage device 122 may correspond to a battery pack, which may have a plurality of clusters of batteries, which may be surrounded by a suitable coolant and a charge controller (not shown). Examples of the power storage device 122 may include, but are not limited to, a lead acid battery, a nickel cadmium battery, a nickel-metal hydride battery, a lithium ion battery, and other rechargeable batteries.

In operation, when the person 104 walks on the outer surface 108a of the body 108, the plurality of sensors 110 (for example the piezoelectric sensors) may generate the electric signal due to the pressure exerted on the outer surface 108a by the walking person 104. The details of the plurality of sensors 110 and the generated electric signal is further described, for example, in FIG. 3. The circuitry 114 may be configured to capture the generated electric signal from one of the plurality of sensors 110 to detect a presence of the person 104 on the outer surface 108a or on one of the plurality of sensors 110. Based on the detected presence of the person 104 and the generated electric signal, the circuitry 114 may be further configured to determine the level of actuation of an actuator of the plurality of actuators 112. In one embodiment, the actuator may be positioned close to the sensor from which the electric signal has been captured. In another embodiment, the actuator may be positioned distant from the sensor from which the electric signal has been captured. The circuitry 114 may further configured to control the actuator of the plurality of actuators 112 based on the determined level of actuation. The detection of presence of the person 104, the determination of the level of actuation, and the control of actuation of the plurality of actuators 112 are further described, for example, in FIG. 3. In some embodiments, the determination of the level of the actuation and the control of the plurality of actuators 112 may depend on the physical and/or medical conditions of the person 104, which may be described further, for example, in FIGS. 3, 4, 5A-5B, and 6. Based on the determined level of actuation, the circuitry 114 may be configured to lift-up or retract-down one of the plurality of actuators 112, to assist gait of the person 104.

Figure 2:
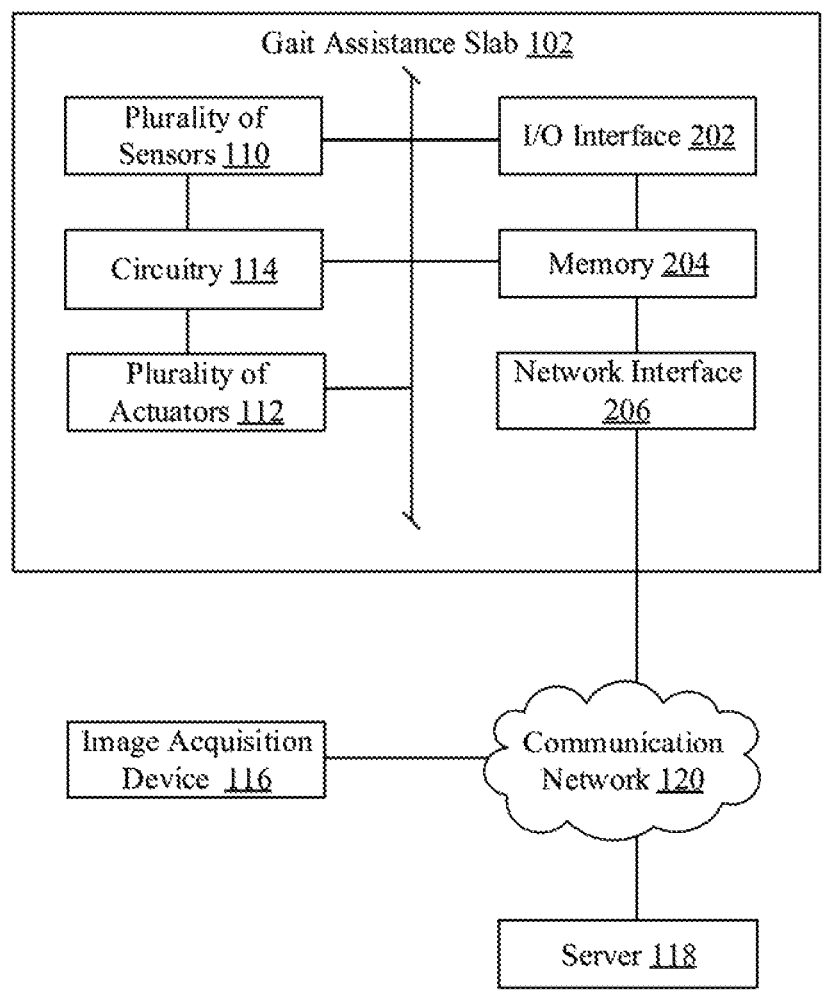
FIG. 2 is a block diagram of the exemplary gait assistance slab of FIG. 1, in accordance with an embodiment of the disclosure.

FIG. 2 is a block diagram of the exemplary gait assistance slab of FIG. 1, in accordance with an embodiment of the disclosure. FIG. 2 is explained in conjunction with elements from FIG. 1. With reference to FIG. 2, there is shown a block diagram 200 of the gait assistance slab 102. In addition to the components (such as the plurality of sensors 110, the plurality of actuators 112, and the circuitry 114) described in the exemplary network environment 100 in FIG. 1, the gait assistance slab 102 may further include an input/output (I/O) interface 202, a memory 204, and a network interface 206 as shown in FIG. 2.

The I/O interface 202 may include suitable logic, circuitry, and interfaces that may be configured to receive an input from the person 104 and provide an output based on the received input. The I/O interface 202 may include various input and output devices, which may be configured to communicate with the circuitry 114. In some embodiments, the I/O interface may be configured to receive information about the medical or physical condition from the person 104 and provide the received information to the circuitry 114 to further control the plurality of actuators 112 and assist gait of the person 104. In some embodiment, the I/O interface 202 may output notification information for the person 104 over the gait assistance slab 102. The notification information may include, but are not limited to, alert with respect to presence or control of the plurality of actuators 112, monitored medical or physical conditions, advertisement information, or other emergency alerts relation to geo-location of the gait assistance slab 102. Examples of the I/O interface 202 may include, but are not limited to, a touch screen, a keyboard, a mouse, a joystick, a microphone, a display device, or a speaker.

The memory 204 may include suitable logic, circuitry, and interfaces that may be configured to store one or more instructions to be executed by the circuitry 114. The memory 204 may be configured to store the level of actuation for the plurality of actuators 112. The memory 204 may be further configured to store physical and medical information of the person 104, which may include, but not limited to, weight information, emotional information, speed information, or gait information. In some embodiments, the memory 204 may be configured to store images captured by the image acquisition device 116 of the person 104 or the gait assistance slab 102. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The network interface 206 may include suitable logic, circuitry, and interfaces that may be configured to facilitate communication between the circuitry 114 and at least one of the image acquisition device 116 or the server 118, or any other device in the exemplary network environment 100, via the communication network 120. The network interface 206 may be implemented by use of various known technologies to support wired or wireless communication of the gait assistance slab 102 with the communication network 120. The network interface 206 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry. The network interface 206 may be configured to communicate via wireless communication with networks, such as the Internet, an Intranet or a wireless network, such as a cellular telephone network, a wireless local area network (LAN), and a metropolitan area network (MAN). The wireless communication may be configured to use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth®, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a protocol for email, instant messaging, and a Short Message Service (SMS).

Figure 3:
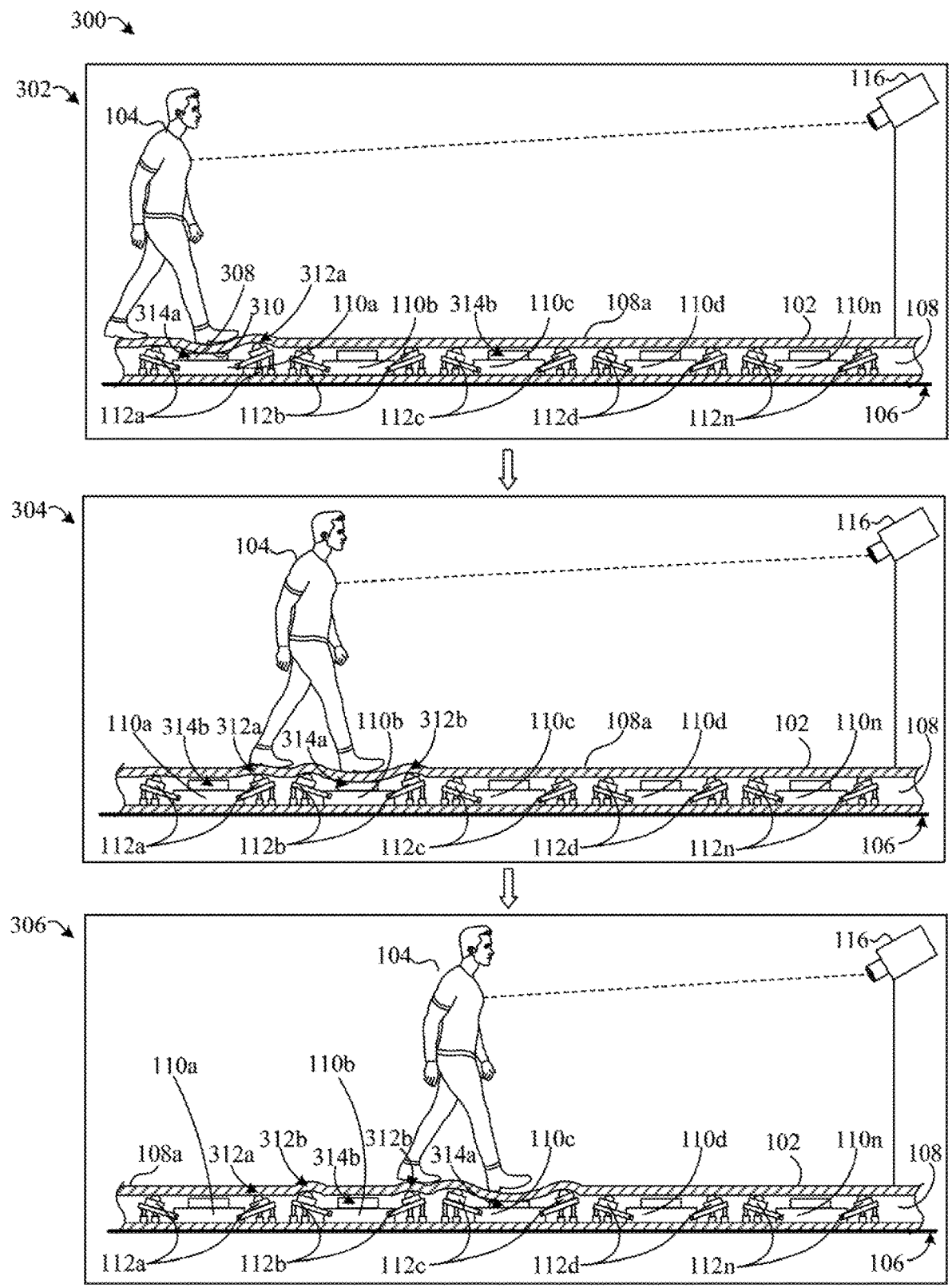
FIG. 3 is a diagram that illustrates exemplary scenarios to provide gait assistance to a person walking on the exemplary gait assistance slab of FIG. 1, in accordance with an embodiment of the disclosure.

FIG. 3 is a diagram that illustrates an exemplary scenario to provide gait assistance to a person walking on the exemplary gait assistance slab of FIG. 1, in accordance with an embodiment of the disclosure. FIG. 3 is explained in conjunction with elements from FIG. 1 and FIG. 2. With reference to FIG. 3, there is shown an exemplary scenario 300 to provide gait assistance to the person 104 walking on the exemplary gait assistance slab 102 that may be disposed on the floor 106.

In the exemplary scenario 300, there is further shown the plurality of sensors 110, in the gait assistance slab 102, that may further include a first sensor 110a, a second sensor 110b, a third sensor 110c, a fourth sensor 110d, and a Nth sensor 110n. The N number of sensors shown in FIG. 3 are presented merely as an example. The plurality of sensors 110 may include only one sensor or more than one sensor for the detection of the person 104, without deviation from the scope of the disclosure. In the exemplary scenario 300, there is further shown the plurality of actuators 112 in the gait assistance slab 102 that may further include a first actuator 112a, a second actuator 112b, a third actuator 112c, a fourth actuator 112d, and a Nth actuator 112n. The N number of actuators shown in FIG. 3 are presented merely as an example. The plurality of actuators 112 may include only one actuator or more than one actuator to assist gait of the person 104, without deviation from the scope of the disclosure. With reference to FIG. 3, when the person 104 walks on the floor 106, the exemplary scenario 300 may be categorized into, but is not limited to, a first stage 302, a second stage 304, and a third stage 306 based on a location of the person 104 on the floor 106.

For example, in the first stage 302, the person 104 may have initiated the walk on the outer surface 108a of the gait assistance slab 102. When the person 104 walks on the outer surface 108a, a portion 308 of each of the plurality of sensors 110 may come in contact with a lower part 310 of the outer surface 108a, such that the pressure or force exerted on the portion 308 of each sensor (for example the first sensor 110a) may generate the electric signal based on the pressure or force applied on the outer surface 108a. For example, when the person 104 walks on the outer surface 108a, the lower part 310 of the outer surface 108a may resiliently deform (as shown in the first stage 302 of FIG. 3), and the portion 308 of the first sensor 110a may come in contact with the lower part 310 of the outer surface 108a, such that the pressure exerted on the portion 308 of the first sensor 110a may activate the first sensor 110a to generate a first electric signal. The first sensor 110a may be configured to send the generated first electric signal to the circuitry 114 of the gait assistance slab 102. In other words, the circuitry 114 may acquire the generated first electric signal from the first sensor 110a (i.e. one of the plurality of sensors 110).

In an embodiment, the circuitry 114 may be further configured to detect the presence of the person 104 based on the first electric signal acquired from the first sensor 110a. The circuitry 114 may be further configured to determine a first level of actuation 312a for the first actuator 112a, based on the detected presence of the person 104 on the portion 308 of the first sensor 110a (or on the outer surface 108a) and further based on an amount of level (for example an amplitude or a peak in volts) of the first electric signal acquired from the first sensor 110a. In some embodiments, the circuitry 114 may select the first actuator 112a from the plurality of actuators 112 for actuation, considering the first actuator 112a is closest or in-proximity to the first sensor 110a from which the first electric signal is acquired. The circuitry 114 may be further configured to control (i.e., activate and lift-up), the first actuator 112a to assist initial gait of the person 104 on the outer surface 108a based on the determined first level of actuation 312a. In some embodiments, the first level of actuation 312a may correspond to a height (for example in millimeter, centimeter, or inches) at which the first actuator 112a may be lifted-up to provide gait assistance to the person 104. For example, the gait assistance provided by the lifted first actuator 112a may correspond to a push being provided to a foot of the person by the first level of actuation 312a as shown in the first stage 302 of FIG. 3. In an embodiment, each of the plurality of actuators 112 may include an inbuilt motor (not shown) which may be activated or deactivated by the circuitry 114 to lift-up or retract-down the corresponding actuator (or a lever of the actuator) to provide the gait assistance to the person 104. In an embodiment, the first level of actuation 312a may be based on the amount of level (for example the amplitude or the peak) of the first electric signal acquired from the corresponding sensor (such as the first sensor 110a). For example, a higher amplitude of the first electric signal may indicate a higher amount of pressure or force applied on the portion 308 (say in case the person 104 is of a higher weight). Therefore, in case of determination of the higher amplitude of the first electric signal acquired from the first sensor 110a, the circuitry 114 may control (i.e. lift) the first actuator 112a to a higher height as compared to a situation when the first electric signal may be of lower amplitude.

In some embodiments, the level of actuation may correspond to a speed or a rate at which a particular actuator may be lifted-up or retracted down based on the control signal received from the circuitry 114. The circuitry 114 may control the speed or rate of actuation of the inbuilt motor of the corresponding actuator (for example the first actuator 112a). For example, in case the speed of the person 104 walking on the outer surface 108a is higher than a predefined threshold (for example 3 Kmph or in miles), then the circuitry 114 may control the first level of actuation 312a of the first actuator 112a at a higher speed as compared to a situation when the walking speed of the person 104 is lower than the predefined threshold. It may be noted that the level of actuation, as height or speed, is presented merely as an example of specific variation of actuations of the plurality of actuators 112. The present disclosure may be also applicable to other types of specific variations of the actuations, without deviation from the scope of the disclosure. The description of other types of specific variations of the actuations has been omitted from the disclosure for the sake of brevity.

In the first stage 302, the person 104 may utilize a lift of the first level of actuation 312a of the first actuator 112a, and may experience a real-time leverage or gait assistance, which may ease the walk of the person 104. Such real-time leverage from the outer surface 108a of the disclosed gait assistance slab 102 may reduce walking fatigue of the person 104. Further, the real-time leverage from the outer surface 108a of the gait assistance slab 102 may even enhance walking speed for a faster movement of the person 104 over the gait assistance slab 102.

In the second stage 304 in FIG. 3, when the person 104 moves away from the first sensor 110a, the outer surface 108a over the first sensor 110a (such as the lower part 310) may be configured to reset from the deformation and release the pressure applied on the first sensor 110a. Upon release of the pressure from the first sensor 110a, the first sensor 110a may reset back to an initial configuration 314b (as shown in the first stage 302 and the second stage 304 in FIG. 3) from an activated configuration 314a (shown in the first stage in FIG. 3). The third sensor 110c and the fourth sensor 110d may also be in the initial configuration 314b with no pressure being exerted on the third sensor 110c and the fourth sensor 110d by the person 104, as shown in the first stage 302 and the second stage 304 of FIG. 3.

As shown in the second stage 304 of FIG. 3, when the person 104 walks further on the outer surface 108a and reaches over the second sensor 110b, the second sensor 110b may be triggered from the initial configuration to the activated configuration to generate a second electric signal. Upon generation of the second electric signal, the second sensor 110b may be configured to send the generated second electric signal to the circuitry 114 of the gait assistance slab 102. The circuitry 114 may be configured to detect the presence of the person 104 over the second sensor 110b based on the second electric signal received from the second sensor 110b. The circuitry 114 may be further configured to determine a second level of actuation 312b for the second actuator 112b, based on the detected presence of the person 104 over the second sensor 110b and the amount of the second electric signal acquired from the second sensor 110b. The second level of actuation 312b for the second actuator 112b shown in the second stage 304 of FIG. 3 and the first level of actuation 312a shown in the first stage 302 of FIG. 3 may be the same or different based on the amount of the acquired second electric signal and the first electric signal, respectively. The circuitry 114 may be further configured to control (i.e., to activate and lift) the second actuator 112b to assist the gait of the person 104 on the outer surface 108a based on the determined second level of actuation 312b, as described in detail, for example, in the first stage 302 for the first actuator 112a.

Further, as shown in the third stage 306 of FIG. 3, when the person 104 moves away from the first actuator 112a, the outer surface 108a adjacent to the first actuator 112a (i.e. first level of actuation 312a) may be configured to reset from the deformation. Further, the circuitry 114 may be configured to deactivate and retract the first actuator 112a to move the first actuator 112a to a deformed or retracted state as shown in the third stage 306 of FIG. 3. Similarly, the fourth actuator 112d may be in the retracted state as the person 104 is not over the fourth sensor 110d during the third stage 306 of FIG. 3. Further, during the third stage 306, when the person 104 moves away from the second sensor 110b and may release the pressure exerted on the second sensor 110b, the second sensor 110b may reset back to the initial configuration 314b from the activated configuration 314a during the second stage 304. Further, as shown in the third stage 306 of FIG. 3, the person 104 may utilize a lift from the second level of actuation 312b of the second actuator 112b, and may experience the real-time leverage or the gait assistance from the second actuator 112b, which may ease the walk of the person 104 and may also reduce walking fatigue of the person 104. Further, the real-time leverage may even enhance walking speed of the person 104.

In accordance with an embodiment, when the person 104 walks on the outer surface 108a of the gait assistance slab 102, the circuitry 114 may be further configured to determine a weight of the person 104 based on the acquired electric signals from one or more of the plurality of sensors 110. For example, based on the pressure or force exerted on the first sensor 110a due to the weight of the person 104 and the generated electric signal, the circuitry 114 may determine the weight of the person 104, like whether the person 104 is a light weight, a medium weight, or a high weight person. Based on the determined weight of the person 104, circuitry 114 may determine the level of actuation (for example, a height or a rate of the lift) of the one of the plurality of actuators 112 (for example, the first actuator 112a). In an embodiment, the circuitry 114 may be further configured to determine a height of the person 104 in addition to the weight of the person 104 based on the acquired electric signal. The height may be either manually entered by the person 104 through the I/O interface 202, or automatically determined based on an image of the person 104 captured by the image acquisition device 116 coupled with the gait assistance slab 102 as shown in FIG. 3. The circuitry 114 may be further configured to estimate a body mass index (BMI) based on the determined height and the weight of the person 104. In case, if the estimated body mass index (BMI) is beyond a threshold value, (for example, if the estimated body mass index (BMI) is beyond 30), the circuitry 114 may identify a medical condition (such as, obesity, or pregnancy, and the like) of the person 104 and may further determine the level of actuation that may be required to control the first actuator 112a or one of the plurality of actuators 112. For example, in case of the identification of the pregnancy condition of the person 104, the height or the rate of lift (i.e. level of actuation) may be lower in comparison to identification of a healthy person with the BMI estimated lower than the threshold value. Based on the determined level of actuation, the circuitry 114 may be further configured to control (i.e. lift) the first actuator 112a or one of the plurality of actuators 112 to assist gait of the person 104 on the outer surface 108a of the gait assistance slab 102.

In another embodiment, when the person 104 walks on the outer surface 108a of the gait assistance slab 102, the circuitry 114 may be further configured to determine timing information associated with a plurality of electric signals acquired from the plurality of sensors 110. Based on the determined timing information, the circuitry 114 may be configured to determine a speed of the person 104 on the outer surface 108a of the body 108. For example, if the person 104 walks and reaches the first sensor 110a at a first time ($T_1$) (i.e. at which the first electric signal may be generated by the first sensor 110a), and if the person 104 walks further and reaches the second sensor 110b at a second time ($T_2$) (i.e. at which the second electric signal may be generated by the second sensor 110b), the timing information may be determined based on a difference between the second time ($T_2$) and the first time ($T_1$). Based on the determined timing information, the circuitry 114 may be further configured to determine the speed of the person 104 on the outer surface 108a based on a ratio of a defined distance between the first sensor 110a and the second sensor 110b (say in feet, yards, or meters) to the determined timing information ($T_2-T_1$). Based on the determined speed of the person 104, the circuitry 114 may be further configured to determine a plurality of actuation levels of the plurality of actuators 112. In some embodiments, the circuitry 114 may determine the level of actuations for the remaining actuators other than the first actuator 112a and the second actuator 112b which are close to the first sensor 110a and the second sensor 110b based on which the speed of the person 104 is determined. For an example, if the person 104 moves at a rapid speed (i.e., when the ratio between the defined distance and the timing information is high), the circuitry 114 may be configured to control the level of actuation of the plurality of actuators 112 at a higher rate (i.e., the movement of lift or retraction of the plurality of actuators 112 may occur in a rapid manner). In another example, if the person 104 moves at a slow speed (i.e., when the ratio between the defined distance and the timing information is less), the circuitry 114 may be configured to control the level of actuation of the plurality of actuators 112 at a minimal rate (i.e., the movement of lift or retraction of the plurality of actuators 112 may occur in a slow manner). Based on the determined plurality of actuation levels for the plurality of actuators 112, the circuitry 114 may be configured to control (i.e. lift or retract) the plurality of actuators 112 to assist gait of the person 104 on the outer surface 108a of the gait assistance slab 102 disposed in the floor 106.

In another embodiment, when the person 104 walks on the outer surface 108a of the gait assistance slab 102, the circuitry 114 may be further configured to control the image acquisition device 116 (for example, a camera) to acquire a plurality of images of the person 104 present on the outer surface 108a of the gait assistance slab 102. The circuitry 114 may also configure or set the image acquisition device 116 to acquire the plurality of images associated of the person 104. The circuitry 114 may configure the image acquisition device 116 to capture or acquire the plurality of images based on a field of view (FOV) of the image acquisition device 116. The FOV of the image acquisition device 116 may include the person 104 and the gait assistance slab 102. Based on the acquired plurality of images, the circuitry 114 may further configured to determine at least one of, gait information, a medical condition, or emotional information of the person 104. The gait information may indicate a walking style of the person 104. The circuitry 114 may be configured to apply one or more image processing techniques (that may be known to the person ordinary skilled in the art) on the acquired plurality of images to determine the medical condition of the person 104. In some embodiments, the medical condition of the person 104 may be manually input to the gait assistance slab 102 through the I/O interface 202 by the person 104 or any other person handling the gait assistance slab 102. Examples of the medical condition may include, but is not limited to, obesity, pregnancy, handicapped, or visual impairment. The details of the one or more image processing techniques known in the art are omitted from the disclosure for the sake of the brevity.

In some embodiments, based on the acquired plurality of images from the image acquisition device 116, the circuitry 114 may be configured to determine the emotional information, which may indicate a current emotional state of the person 104 during the travel on the outer surface 108a of the gait assistance slab 102. For the determination of the emotional information or the emotional state, the image acquisition device 116 may be configured to capture the plurality of images of the person 104 over a specific time period. The captured plurality of images may be utilized to determine a facial expression of the person 104. The facial expression may indicate one or more motions or positions of muscles of a face of the person 104, where the facial expressions may manifest an emotion. The muscles of the face may move the skin of the person 104, or may create facial lines/folds, or may even cause the movement of facial features, such as mouth, head, nose, eye, eyebrows of the person 104. The circuitry 114 may be configured to determine the emotional state of the person 104 based on the determined facial expression of the person 104. The plurality of categories of emotional state of the person 104 may include, but are not limited to, a happy state, a sad state, an angry state, a calm state, a fear state, a neutral state, an excited state, a confused state, a stressed state, a disgusted state, a nervous state, a disturbed state, a tired state, a sleep state, or a scared state.

The circuitry 114 may be further configured to determine the level of actuation of the one of the plurality of actuators 112 (for example, the first actuator 112a, or the second actuator 112b) based on the determined gait information, the medical condition, or the emotional information of the person 104. In one example, in case the person 104 slips on the floor 106 while walking on the outer surface 108a or may be handicapped (i.e. walking style), such slip or walking style of the person 104 may be captured by the image acquisition device 116 as the gait information. The disclosed gait assistance slab 102 may further assist or stabilize the walk of the person 104 with the controlled level of actuations (i.e. control of the height or the rate of lift/retraction) of the plurality of actuators 112 in accordance with determined gait information. For example, for the handicapped person, the level of actuation may correspond to a lower height or rate of actuations of the plurality of actuators 112.

In another example, in case of determination that the person 104 is emotionally disturbed, such as, stressed, nervous, or confused, and the like, during the travel over the gait assistance slab 102, such stressed, nervous, or confused emotional states may be captured by the image acquisition device 116 as the emotional information. The circuitry 114 may further be configured to assist or stabilize the walk of the person 104 with the level of actuations (for example reduction of the height or the rate of lift/retraction) of the plurality of actuators 112 to alleviate emotional disturbance of the person 104 while walking in accordance with the determined emotional information of the person 104.

In yet another example, in case the person 104 has specific medical condition, such as an obesity or a pregnancy, as the determined medical condition, the circuitry 114 may assist or stabilize the walk of the person 104 with the reduction in the height or the rate of lift/retraction (i.e. level of actuation) of the plurality of actuators 112. In an embodiment, in case of the medical condition as pregnancy (for example), the circuitry 114 may not control or lift-up the plurality of actuators 112 (i.e. level of actuation near to zero) to avoid an accident with the person 104 walking over the gait assistance slab 102. Therefore, the circuitry 114 may be configured to control at least one of the plurality of actuators 112 based on the determined level of actuations in accordance with the determined gait information, emotional information, or the medical condition, and provide a real-time and enhanced assistance to the gait of the person 104 on the outer surface 108a of the gait assistance slab 102.

Figure 4:
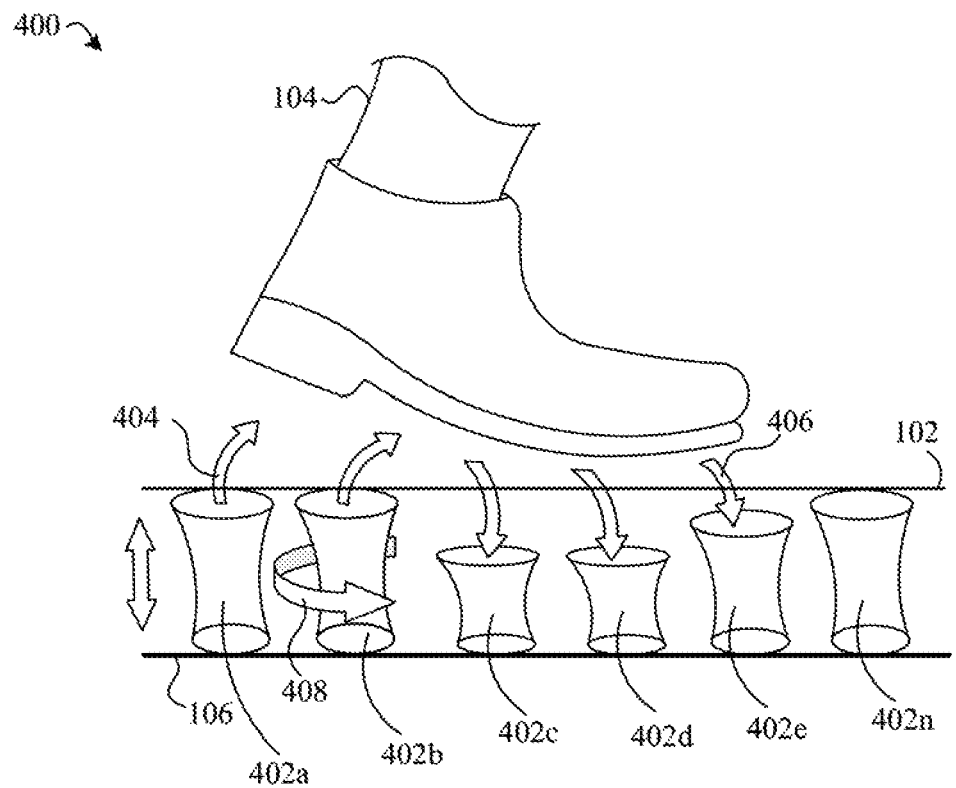
FIG. 4 is a diagram that illustrates a perspective view of a plurality of actuators in an exemplary gait assistance slab, in accordance with an embodiment of the disclosure.

FIG. 4 is a diagram that illustrates a perspective view of a plurality of actuators in an exemplary gait assistance slab, in accordance with an embodiment of the disclosure. FIG. 4 is explained in conjunction with elements from FIG. 1, FIG. 2, and FIG. 3. With reference to FIG. 4, there is shown a perspective view 400 of a plurality of actuators 402 in the gait assistance slab 102. The plurality of actuators 402 may have the same functions as the plurality of actuators 112 of FIG. 1 and FIG. 3. However, the plurality of actuators 402 may be structurally different from the plurality of actuators 112 of FIG. 1 and FIG. 3. Referring to FIG. 4, the plurality of actuators 402 may include a first actuator 402a, a second actuator 402b, a third actuator 402c, a fourth actuator 402d, a fifth actuator 402e, and a Nth actuator 402n. The number of the plurality of actuators 402 shown in FIG. 4 are presented merely as an example. The plurality of actuators 402 may also include only one actuator or more than one actuator to assist gait of the person 104, without deviation from the scope of the disclosure. It may be noted here that the orientations, arrangements, or shapes of the plurality of actuators 402 shown in FIG. 4 are presented merely as an example. The present disclosure may be also applicable to other orientations, arrangements, or shapes of the plurality of actuators 402, without deviation from the scope of the disclosure.

Referring to FIG. 4, when the person 104 walks on the outer surface 108a of the gait assistance slab 102 disposed on the floor 106, the plurality of actuators 402 may act as a suspension system for the person 104, and may include a series of tubes that may compress or rebound in a defined manner, as shown in FIG. 4. For example, the first actuator 402a and the second actuator 402b may rebound (i.e., lifted-up as 404 in FIG. 4) away from the floor 106. In another example, the third actuator 402c, the fourth actuator 402d, and the fifth actuator 402e may be compressed (i.e., retracted down as 406 in FIG. 4) towards the floor 106. The circuitry 114 may be configured to control the rebound or compression of the plurality of actuators 402 in up and down directions based on the level of actuations as described, for example, in FIG. 3 for the plurality of actuators 112. For example, there may be 50-100 number of actuators (i.e. the plurality of actuators 402) per square feet area in the gait assistance slab 102. Such structure of the plurality of actuators 402 may effectively control the gait of the person 104 to provide effective gait assistance to the person 104. In some embodiments, the plurality of actuators 402 may include an assistive device, such as a motor (not shown), at a bottom of the plurality of actuators 402, so that the plurality of actuators 402 may rebound (i.e. lifted-up) or compress (i.e. retracted down) based on the control provided by the circuitry 114, so that the person 104 may not feel exhausted during the walk. In certain situations, the person 104 may trip and slip on the gait assistance slab 102 based on his/her walking style or speed of the walk. To avoid such situations, the plurality of actuators 402 may even adapt a twisted configuration 408 to stabilize (i.e., twisting the plurality of actuators 402 in opposite direction of the slip of the person 104) the movement of walk of the person 104.

FIGS. 5A and 5B are diagrams that collectively illustrate an exemplary scenario of gait assistance on an inclined surface, by the gait assistance slab of FIG. 1, in accordance with an embodiment of the disclosure. FIGS. 5A and 5B are explained in conjunction with elements from FIGS. 1, 2, 3 and 4. With reference to FIGS. 5A and 5B, there is shown the gait assistance slab 102, which is disposed on the floor 106 in an inclined surface (for example, an inclined road, or an inclined pathway, and the like). In FIG. 5A, there is shown a downhill scenario 500, where the person 104 may walk towards a downhill of the floor 106. In FIG. 5B, there is shown an uphill scenario 502, where the person 104 may walk towards an uphill of the floor 106.

With reference to FIGS. 5A-5B, the circuitry 114 of the gait assistance slab 102 may be configured to control the image acquisition device 116 to acquire a first image of the person 104 present on the outer surface 108a of the gait assistance slab 102 and acquire a second image of the gait assistance slab 102. The field of view (FOV) of the image acquisition device 116 may be set in a direction, such that the first image of the person 104 and the second image of the gait assistance slab 102 may be acquired or captured accurately by the image acquisition device 116. Based on the acquired second image of the gait assistance slab 102, the circuitry 114 may determine a presence of the gait assistance slab 102 on an inclined surface of the floor 106. Further, based on the acquired first image, the circuitry 114 may determine a direction of movement of the person 104 on the outer surface 108a of the gait assistance slab 102. The direction of movement of the person 104 may include at least one of the downhill or the uphill. In other words, the direction of movement of the person 104 may indicate whether the person 104 is moving down or up on the gait assistance slab 102 located on the inclined surface of the floor 106. The circuitry 114 may be further configured to determine the level of actuation of the one or more of the plurality of actuators 112 based on the determined presence of the gait assistance slab 102 on the inclined surface and the determined direction of movement of the person 104. The circuitry 114 may be further configured to control, based on the determined level of actuation, one or more of the plurality of actuators 112 (as described, for example, in FIG. 3) to assist the gait of the person 104 on the outer surface 108a of the gait assistance slab 102 that is disposed on the inclined surface of the floor 106.

With reference to FIG. 5A, there is shown the downhill scenario 500, which depicts the direction of movement of the person 104 on the floor 106 along the downhill. In the downhill scenario 500, for example, the circuitry 114 may be further configured to control the power storage device 122 to store power associated with the electric signals acquired from the plurality of sensors 110 when the person 104 walks over the outer surface 108a. The power storage device 122 may be coupled to the gait assistance slab 102 and may be configured to provide the stored power to the circuitry 114 and the plurality of actuators 112 to either lift or retract for the gait assistance of the person 104. In some embodiments, the power storage device 122 may be an integral part of the gait assistance slab 102 which may be used to provide power to each electric component of the gait assistance slab 102. In an embodiment, in the downhill scenario 500, the plurality of actuators 112 may be configured to be deactivated and retracted based on the determined presence of the gait assistance slab 102 on the inclined surface and the determined direction of movement of the person 104. As the plurality of actuators may be deactivated during the downhill travel of the person 104, the acquired electric signals from the plurality of sensors 110 may not be utilized for activation of the plurality of actuators 112, and such unutilized electric signals may be stored in the power storage device 122.

With reference to FIG. 5B, there is shown the uphill scenario 502, which depicts the direction of movement of the person 104 on the floor 106 along the uphill. The circuitry 114 may determine that the person 104 is walking along the uphill based on the acquired first image and the second image, and accordingly control the plurality of actuators 112 to be activated and lifted-up, to leverage the gait of the person 104 along the uphill. Thus, the disclosed gait assistance slab 102 may provide the gait assistance to the person 104 moving in the uphill direction based on control of the one or more of the plurality of actuators 112. In an embodiment, the gait assistance slab 102 may control the power storage device 122 to store the power of the acquired electric signals generated due to movement of a first person along the downhill on the gait assistance slab 102, and simultaneously control the actuation of the plurality of actuators 112 with the stored power to provide gait assistance to a second person moving along the uphill on the gait assistance slab 102. The second person may be different from the first person. Thus, the disclosed gait assistance slab 102 may be a smart gait assistance device which may dynamically control the storage of power and simultaneously control the utilization of the stored power for gait assistance, based on different situations (i.e. uphill or downhill) detected for different people (for example, the person 104) based on run-time acquisition of the first image and the second image.

In accordance with an embodiment, the circuitry 114 may also be configured to control level of actuations of the plurality of actuators 112 based on traffic information (for example, a congestion of persons or other objects on the gait assistance slab 102. For example, in case of determination of a congestion of persons or objects in the downhill scenario 500 (i.e. based on images captured by the image acquisition device 116), the circuitry 114 may control the level of actuations (such as increase the level of actuations to a higher rate or speed of lift and retraction of the plurality of actuators 112) to relieve congestion of the persons on the gait assistance slab 102. In another example, in case of determination of no congestion of persons or objects in the uphill scenario 502, the circuitry 114 may control the level of actuations (such as increase the level of actuations to a maximal rate or a maximal height of lift and retraction of the plurality of actuators 112) to improve speed of movement of the persons (like person 104) and reduce walking fatigue over the disclosed gait assistance slab 102.

Figure 6:
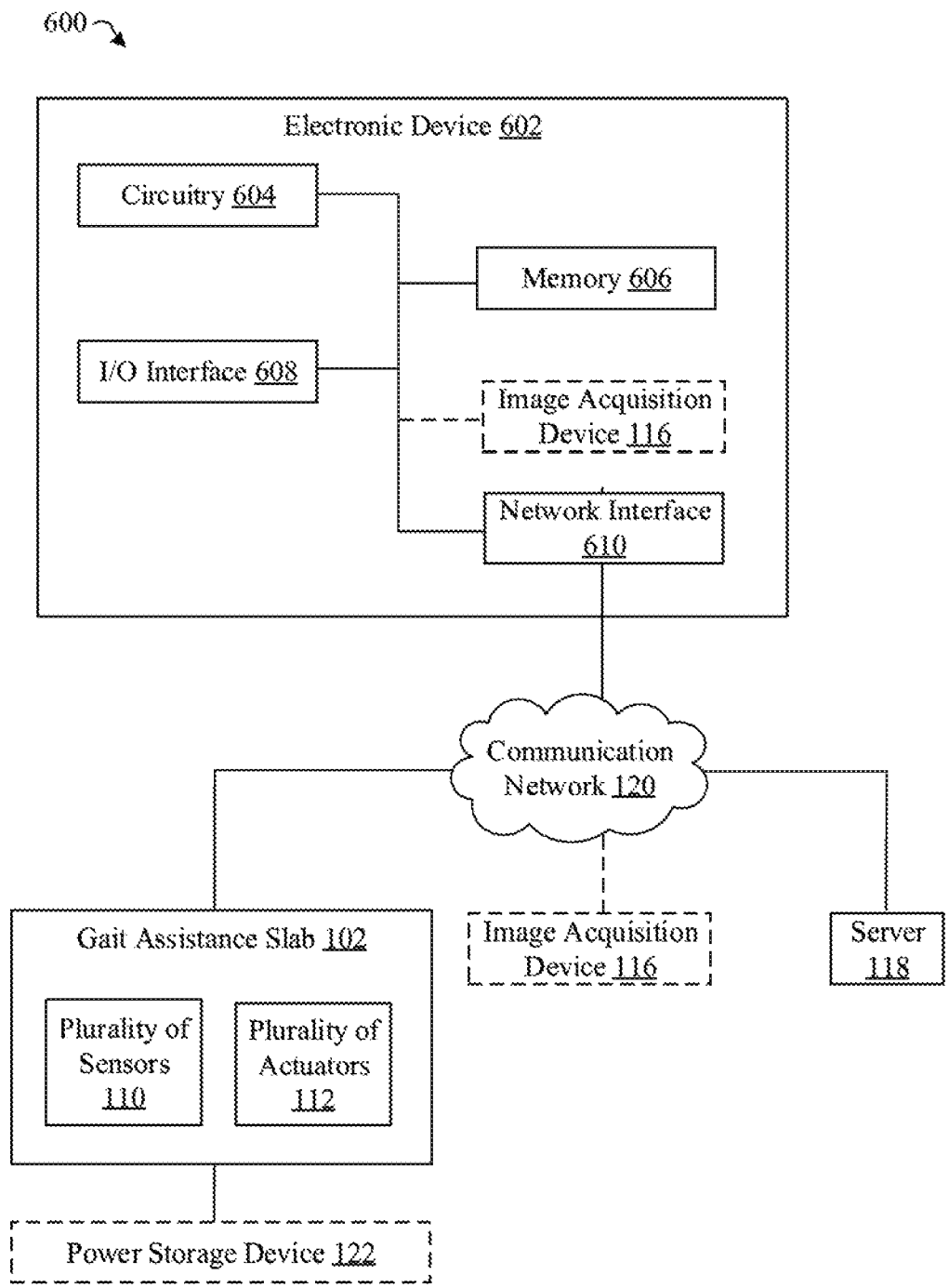
FIG. 6 is a block diagram that illustrates an electronic device communicatively coupled with the gait assistance slab of FIG. 1 to provide gait assistance, in accordance with an embodiment of the disclosure.

FIG. 6 is a block diagram that illustrates an electronic device communicatively coupled with the gait assistance slab of FIG. 1 to provide gait assistance, in accordance with an embodiment of the disclosure. FIG. 6 is explained in conjunction with elements from FIGS. 1, 2, 3, 4, 5A, and 5B. With reference to FIG. 6, there is shown a block diagram 600 of an electronic device 602. The electronic device 602 may include circuitry 604, a memory 606, an input/output (I/O) interface 608, and a network interface 610. The network interface 610 may be communicatively coupled to the gait assistance slab 102, the image acquisition device 116, and the server 118. In some embodiment, the image acquisition device 116 may be an integral part of the electronic device 602. The gait assistance slab 102 may be coupled with the power storage device 122 (for example battery), so that the power storage device 122 may provide power to the plurality of sensors 110, the plurality of actuators 112, and other components of the gait assistance slab 102, that may be located inside the gait assistance slab 102.

In an embodiment, the electronic device 602 may include suitable logic, circuitry, interfaces, and/or code that may be configured to control the gait assistance slab 102, the image acquisition device 116, and the power storage device 122 to provide gait assistance to a person (for example the person 104) walking over the outer surface 108a of the gait assistance slab 102. Examples of the electronic device 602 may include, but is not limited to, a controller device, a computer, a mobile phone, a smart phone, a laptop, a personal digital assistance (PDA), a server (such as the server 118), a mainframe system, or any computing device.

The electronic device 602 may be configured to receive the electric signals acquired by the plurality of sensors 110 of the gait assistance slab 102, via the communication network 120, when the person 104 (not shown in FIG. 6) walks on the outer surface 108a of the gait assistance slab 102. The electronic device 602 may be further configured to detect the presence of the person 104 on the outer surface 108a based on the received electric signal acquired from one or more of the plurality of sensors 110. The detection of the presence of the person 104 on the outer surface 108a is described, in detail, for example, in FIG. 3. The electronic device 602 may be further configured to determine the level of actuation of one of the plurality of actuators 112 disposed inside the body 108 of the gait assistance slab 102. The determination of the level of actuation is described, in detail, for example, in FIG. 3. The electronic device 602 may be further configured to transmit information about the determined level of actuation to the gait assistance slab 102, wherein the gait assistance slab 102 may control the one of the plurality of actuators 112 based on the received information to assist gait of the person 104 on the outer surface 108a. The control of one of the plurality of actuators 112 is described, in detail, for example, in FIG. 3.

The circuitry 604 may include suitable logic, circuitry, and interfaces that may be configured to execute program instructions associated with different operations to be executed by the electronic device 602. For example, some of the operations may include, but is not limited to, reception of the electric signal acquired from one of the plurality of sensors 110 disposed inside the body 108 of the gait assistance slab 102, detection of the presence of a person 104 on the outer surface 108a based on the received electric signal acquired from one of the plurality of sensors 110, determination of the level of actuation of one of the plurality of actuators 112 based on the detected presence of the person 104 and the electric signal, and transmission of the information about the determined level of actuation to the gait assistance slab 102. The gait assistance slab 102 may control the one of the plurality of actuators 112 based on the received information from the electronic device 602 to assist gait of the person 104 on the outer surface 108a of the gait assistance slab 102 disposed on the floor 106. In some embodiments, the circuitry 604 may be communicatively coupled to the plurality of sensors 110 and the plurality of actuators 112 of the gait assistance slab 102 and may control different operations to be executed by the gait assistance slab 102.

The circuitry 604 may include one or more specialized processing units, which may be implemented as a separate processor. In an embodiment, the one or more specialized processing units may be implemented as an integrated processor or a cluster of processors that perform the functions of the one or more specialized processing units, collectively. The circuitry 604 may be implemented based on a number of processor technologies known in the art. Examples of implementations of the circuitry 604 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), a Programmable Logical Control (PLC) Unit, and/or other control circuits. In an embodiment, the circuitry 604 may be further configured to control the image acquisition device 116 to acquire medical, emotional, or gait information of the person 104 and accordingly determine the level of actuation as described, for example, in FIG. 3.

The circuitry 604 may be further configured to control the power storage device 122 to store power associated with the acquired electric signals from the plurality of sensors 110. The power storage device 122 may be coupled to the gait assistance slab 102 and may be configured to provide the stored power to the plurality of actuators 112 of the gait assistance slab 102. The control of the power storage device 122 is described, in detail, for example, in FIG. 1

In other embodiment, the circuitry 604 may be configured to determine the weight of the person 104 based on the received electric signal. The circuitry 604 may be further configured to determine the level of actuation of the one of the plurality of actuators 112 based on the determined weight of the person 104 and transmit the information about the determined level of actuation to the gait assistance slab 102. The determination of the weight of the person 104 is described, in detail, for example, in FIG. 3.

The electronic device 602 may further include the image acquisition device 116 that may be configured to acquire a plurality of images of the person 104 present on the outer surface 108a of the gait assistance slab 102. The electronic device 602 may be further configured to determine at least one of the medical condition, the emotional information, or the gait information of the person 104, based on the acquired plurality of images. The determination of at least one of the medical condition, the emotional information, or the gait information of the person 104 is described, for example, in FIG. 3. The electronic device 602 may be further configured to determine the level of actuation of the one of the plurality of actuators 112 based on the determined at least one of the medical condition, the emotional information, or the gait information of the person 104. The electronic device 602 may be further configured to transmit the information about the determined level of actuation to the gait assistance slab 102 to provide gait assistance to the person 104 based on the determined medical condition, the emotional information, or the gait information, as described, for example, in FIG. 3.

The circuitry 604 may be further configured to determine the speed of the person 104 based on the timing information $(T_2-T_1)$ associated with the plurality of electric signals acquired from the plurality of sensors 110. The circuitry 604 may be further configured to determine the plurality of actuation levels of the plurality of actuators 112 based on the determined speed. The circuitry 604 may be further configured to transmit the information about the determined plurality of actuation levels to the gait assistance slab 102. The determination of the speed of the person 104 and the determination of the level of actuations based on the speed is described, for example, in FIG. 3. The circuitry 114 of the gait assistance slab 102 may further control the plurality of actuators 112 based on the information received from the circuitry 604 of the electronic device 602.

The functions of the memory 606, the I/O interface 608, and the network interface 610 of FIG. 6 may be the same as the functions of the memory 204, I/O interface 202, and the network interface 206 described, for example, in FIG. 1. Therefore, the description of the memory 606, the I/O interface 608, and the network interface 610 are omitted from the disclosure for the sake of brevity.

Figure 7:
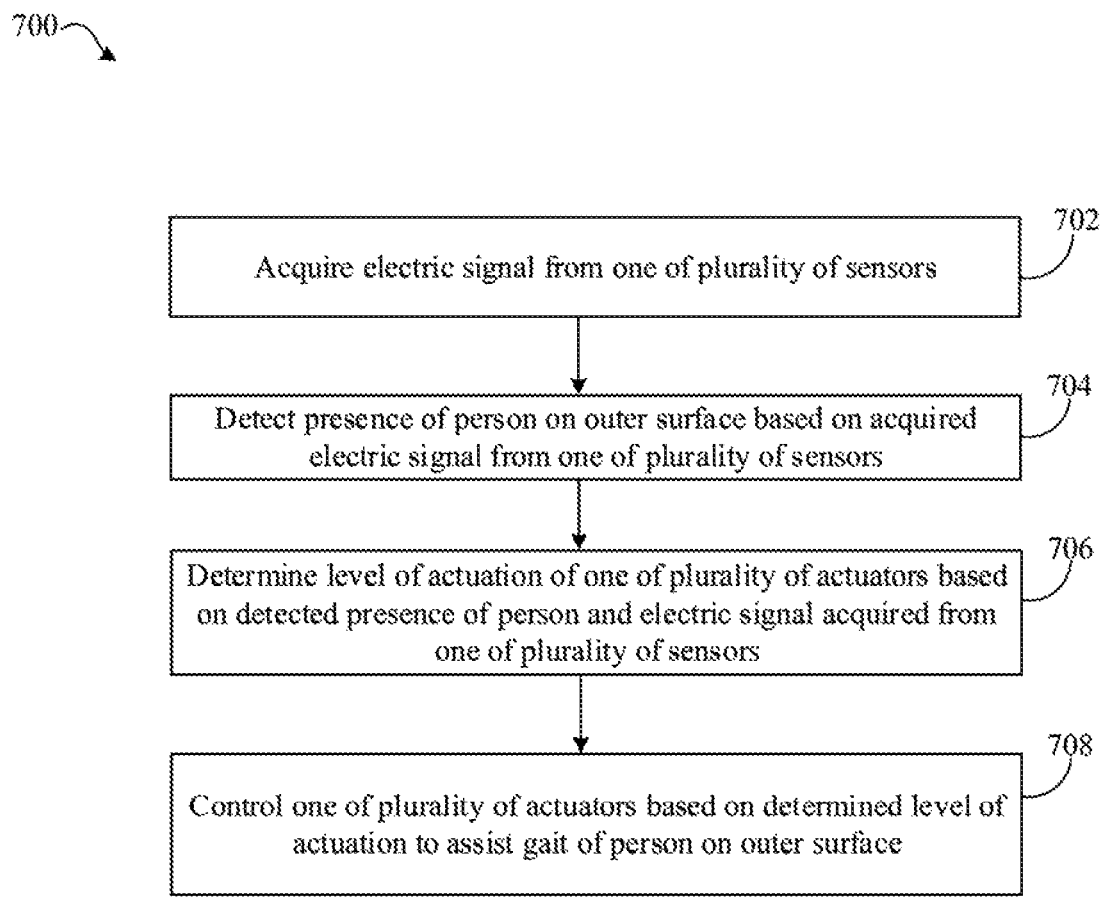
FIG. 7 is a flowchart that illustrates an exemplary method to provide gait assistance, in accordance with an embodiment of the disclosure.

FIG. 7 is a flowchart that illustrates an exemplary method to provide gait assistance, in accordance with an embodiment of the disclosure. FIG. 7 is explained in conjunction with elements from FIGS. 1, 2, 3, 4, 5A, 5B, and 6. With reference to FIG. 7, there is shown a flowchart 700 that depicts a method to provide gait assistance to a person 104 of FIG. 1. The method may include operations from 702 to 708 that may be implemented, for example, by the gait assistance slab 102 or the circuitry 114 of FIG. 2. The method illustrated in the flowchart 700 may start from 702.

At 702, the electric signal may be acquired from one of the plurality of sensors 110. In an embodiment, the circuitry 114 may be configured to acquire the electric signal from one of the plurality of sensors 110 as described, for example, in FIG. 3.

At 704, the presence of the person 104 on the outer surface 108a may be detected based on the acquired electric signal from one of the plurality of sensors 110. In an embodiment, the circuitry 114 may be configured to detect the presence of the person 104 on the outer surface 108a (or on one of the plurality of sensors 110) based on the electric signal acquired from the one of the plurality of sensors 110 (for example the first sensor 110a), as described, for example, in FIG. 3.

At 706, the level of actuation may be determined for one of the plurality of actuators 112 based on the detected presence of the person 104 and the electric signal acquired from one of the plurality of sensors 110. In an embodiment, the circuitry 114 may be configured to determine the level of actuation for one of the plurality of actuators 112 (for example the first actuator 112a close to the first sensor 110a) based on the detected presence of the person 104 and amount of the electric signal acquired from one of the plurality of sensors 110 (for example, the first sensor 110a), as described, for example, in FIG. 3.

At 708, one of the plurality of actuators may be controlled, based on the determined level of actuation, to assist gait of the person 104 on the outer surface 108a. In an embodiment, the circuitry 114 may be configured to control one of the plurality of actuators 112 (for example the first actuator 112a) based on the determined level of actuation, to assist gait of the person 104 on the outer surface 108a, as described, for example, in FIG. 3. Control may pass to end.

The flowchart 700 is illustrated as discrete operations, such as 702, 704, 706, and 708. However, in certain embodiments, such discrete operations may be further divided into additional operations, combined into fewer operations, or eliminated, depending on the implementation without detracting from the essence of the disclosed embodiments.

Various embodiments of the disclosure may provide a non-transitory computer readable medium and/or storage medium having stored thereon, instructions executable by a machine and/or a computer to operate a gait assistance slab. The instructions may cause the machine and/or computer (for example the electronic device 602 in FIG. 6) to perform operations that may include reception of an electric signal acquired from one of a plurality of sensors disposed inside a body of a gait assistance slab. The body may include an outer surface. The operations may further include detection of a presence of a person on the outer surface based on the received electric signal acquired from the one of the plurality of sensors. The operations may further include determination of a level of actuation of one of a plurality of actuators disposed inside the body of the gait assistance slab. The operations may further include transmission of information about the determined level of actuation to the gait assistance slab, where the gait assistance slab controls the one of the plurality of actuators based on the received information to assist gait of the person on the outer surface.

For the purposes of the present disclosure, expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural. Further, all joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

The foregoing description of embodiments and examples has been presented for purposes of illustration and description. It is not intended to be exhaustive or limiting to the forms described. Numerous modifications are possible considering the above teachings. Some of those modifications have been discussed and others will be understood by those skilled in the art. The embodiments were chosen and described for illustration of various embodiments. The scope is, of course, not limited to the examples or embodiments set forth herein but can be employed in any number of applications and equivalent devices by those of ordinary skill in the art. Rather it is hereby intended the scope be defined by the claims appended hereto. Additionally, the features of various implementing embodiments may be combined to form further embodiments.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted for carrying out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions. It may be understood that, depending on the embodiment, some of the steps described above may be eliminated, while other additional steps may be added, and the sequence of steps may be changed.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system with an information processing capability to perform a particular function either directly, or after either or both of the following: a) conversion to another language, code or notation; b) reproduction in a different material form. While the present disclosure has been described with reference to certain embodiments, it will be understood by those skilled in the art that various changes may be made, and equivalents may be substituted without departing from the scope of the present disclosure. In addition, many modifications may be made to adapt a situation or material to the teachings of the present disclosure without departing from its scope. Therefore, it is intended that the present disclosure may not be limited to the embodiment disclosed, but that the present disclosure will include all embodiments that fall within the scope of the appended claims.

What is claimed is:

1. A gait assistance slab, comprising:
   a body including an outer surface;
   a plurality of sensors disposed inside the body;
   a plurality of actuators disposed inside the body; and
   circuitry communicatively coupled to the plurality of sensors and the plurality of actuators, wherein the circuitry is configured to:
      detect a presence of a person on the outer surface based on an electric signal acquired from one of the plurality of sensors,
      determine a level of actuation of one of the plurality of actuators based on the detected presence of the person and the electric signal acquired from the one of the plurality of sensors, and
      control, based on the determined level of actuation, the one of the plurality of actuators to assist gait of the person on the outer surface;
   wherein the gait assistance slab is coupled to a floor; and
   wherein the outer surface of the body is formed of a resiliently deformable material.

2. The gait assistance slab according to claim 1, wherein to control the one of the plurality of actuators, the circuitry is configured to lift or retract the one of the plurality of actuators, based on the determined level of actuation.

3. The gait assistance slab according to claim 1, wherein the body is substantially square or a rectangular profile.

4. The gait assistance slab according to claim 1, wherein the plurality of sensors correspond to piezoelectric sensors arranged in a first pattern inside the body,
   wherein the circuitry is further configured to control a power storage device to store power associated with the acquired electric signal, and
   wherein the power storage device is coupled to the gait assistance slab and configured to provide the stored power to the circuitry and the plurality of actuators.

5. The gait assistance slab according to claim 1, wherein the plurality of actuators are arranged in a second pattern inside the body, and wherein the plurality of actuators include at least one of: a mechanical actuator, an electro-mechanical actuator, a hydraulic actuator, or a pneumatic actuator.

6. The gait assistance slab according to claim 1, wherein the circuitry is further configured to:
   determine a weight of the person based on the acquired electric signal;
   determine the level of actuation of the one of the plurality of actuators based on the determined weight of the person; and
   control, based on the determined level of actuation, the one of the plurality of actuators to assist the gait of the person on the outer surface.

7. The gait assistance slab according to claim 1, wherein the circuitry is further configured to:
   control an image acquisition device to acquire a plurality of images of the person present on the outer surface;
   determine at least one of: a medical condition, emotional information, or gait information of the person, based on the acquired plurality of images;
   determine the level of actuation of the one of the plurality of actuators based on the determined at least one of: the medical condition, the emotional information, or the gait information of the person; and
   control, based on the determined level of actuation, the one of the plurality of actuators to assist the gait of the person on the outer surface.

8. The gait assistance slab according to claim 1, wherein the circuitry is further configured to:
   determine a speed of the person on the outer surface based on timing information associated with a plurality of electric signals acquired from the plurality of sensors;
   determine a plurality of actuation levels of the plurality of actuators based on the determined speed of the person; and
   control, based on the determined plurality of actuation levels, the plurality of actuators to assist the gait of the person on the outer surface.

9. The gait assistance slab according to claim 1, wherein the circuitry is further configured to:

control an image acquisition device to acquire a first image of the person present on the outer surface of the gait assistance slab and acquire a second image of the gait assistance slab;
determine a presence of the gait assistance slab on an inclined surface based on the acquired second image and a direction of movement of the person on the outer surface based on the acquired first image, wherein the direction of movement includes at least one of: a downhill or an uphill;
determine the level of actuation of the one of the plurality of actuators based on the determined presence of the gait assistance slab on the inclined surface and the determined direction of movement of the person; and
control, based on the determined level of actuation, the one of the plurality of actuators to assist the gait of the person on the outer surface.

10. The gait assistance slab according to claim 9, wherein in case the determined direction of movement of the person is the downhill, the circuitry is further configured to control a power storage device to store power associated with the acquired electric signal, and
wherein the power storage device is coupled to the gait assistance slab and configured to provide the stored power to the circuitry and the plurality of actuators.

11. A method, comprising:
in a gait assistance slab, which includes a body including an outer surface, a plurality of sensors disposed inside the body, a plurality of actuators disposed inside the body, and circuitry communicatively coupled to the plurality of sensors and the plurality of actuators, wherein the gait assistance slab is coupled to a floor and wherein the outer surface of the body is formed of a resiliently deformable material:
acquiring, by the circuitry, an electric signal from one of the plurality of sensors;
detecting, by the circuitry, a presence of a person on the outer surface based on the acquired electric signal from the one of the plurality of sensors;
determining, by the circuitry, a level of actuation of the one of the plurality of actuators based on the detected presence of the person and the electric signal acquired from the one of the plurality of sensors; and
controlling, by the circuitry, the one of the plurality of actuators based on the determined level of actuation to assist gait of the person on the outer surface.

12. The method according to claim 11, further comprising:
controlling, by the circuitry, a power storage device to store power associated with the acquired electric signal, wherein the power storage device is coupled to the gait assistance slab and configured to provide the stored power to the circuitry and the plurality of actuators.

13. The method according to claim 11, wherein the plurality of actuators are arranged in a second pattern inside the body, and wherein the plurality of actuators include at least one of: a mechanical actuator, an electro-mechanical actuator, a hydraulic actuator, or a pneumatic actuator.

14. The method according to claim 11, wherein the controlling the one of the plurality of actuators, further comprising lifting or retracting the one of the plurality of actuators based on the determined level of actuation.

* * * * *